United States Patent [19]

Terahara et al.

[11] Patent Number: 4,537,859
[45] Date of Patent: * Aug. 27, 1985

[54] PROCESS FOR PREPARING 3-HYDROXY-ML-236B DERIVATIVES KNOWN AS M-4 AND M-4'

[75] Inventors: Akira Terahara; Minoru Tanaka, both of Hiromachi, Japan

[73] Assignee: Sankyo Company, Limited, Tokyo, Japan

[*] Notice: The portion of the term of this patent subsequent to Oct. 18, 2000 has been disclaimed.

[21] Appl. No.: 442,840

[22] Filed: Nov. 18, 1982

[30] Foreign Application Priority Data

Nov. 20, 1981 [JP] Japan .................. 56-186641

[51] Int. Cl.³ .......... C12P 7/42; C12P 7/62; C12N 1/20
[52] U.S. Cl. .................. 435/146; 435/135; 435/253; 435/872
[58] Field of Search .......... 435/135, 136, 146, 253

[56] References Cited

U.S. PATENT DOCUMENTS 3,281,330 10/1966 Fonken et al. .............. 435/136
3,392,171  7/1968 Fonken et al. .............. 435/121
4,410,629 10/1983 Terahara et al. .............. 435/135

*Primary Examiner*—Alvin E. Tanenholtz
*Attorney, Agent, or Firm*—Frishauf, Holtz, Goodman & Woodward

[57] ABSTRACT

Compounds of formula (I):

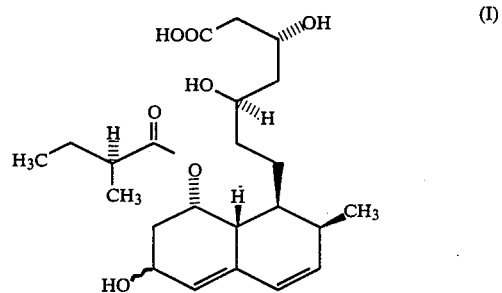

(wherein ∼∼OH represents ▬OH or ⦀OH), that is to say M-4 carboxylic acid and M-4' carboxylic acid, as well as pharmaceutically acceptable salts and esters thereof and the corresponding ring-closed lactones may be prepared by contacting an ML-236B compound with a microorganism of the genus Nocardia or a cell-free, enzyme-containing extract thereof and then, if necessary, subjecting the resulting product to one or more of the following reactions: hydrolysis, salification, esterification and lactonisation. The resulting M-4 and M-4' derivatives have the ability to inhibit the biosynthesis of cholesterol and are therefore of value in the therapy and/or prophylaxis of hyperlipaemia and arteriosclerosis.

22 Claims, No Drawings

PROCESS FOR PREPARING 3-HYDROXY-ML-236B DERIVATIVES KNOWN AS M-4 AND M-4'

BACKGROUND TO THE INVENTION

The present invention relates to a process for preparing certain 3-hydroxy-ML-236B derivatives known as M-4 and M-4', as well as salts and esters of these compounds.

ML-236B, which can exist in the form of an acid (known as "ML-236B carboxylic acid") or a lactone (known as "ML-236B lactone"), is disclosed in United Kingdom Patent Specification No. 1,453,425 and, in its lactone form, has the formula:

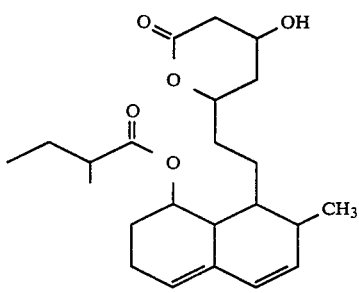

Subsequently, United Kingdom Patent Specification No. 1,555,831 disclosed a variety of salts and esters of ML-236B. ML-236B and its salts and esters were found to inhibit the biosynthesis of cholesterol by competing with 3-hydroxy-3-methylglutaryl coenzyme A reductase, which is the rate-determining enzyme for chloesterol biosynthesis; these compounds were thus found to exhibit a very marked ability to reduce serum cholesterol levels.

Subsequently, certain 3-hydroxy-ML-236B derivatives were isolated as products of the animal metabolism of ML-236B lactone and similar derivatives were found to be produced by the enzymatic hydroxylation of ML-236B lactone or carboxylic acid or salts or esters thereof, effected by means of various microorganisms of the genera Absidia, Cunninghamella, Syncephalastrum, Streptomyces, Mucor, Rhizopus, Zygorinchus, Circinella, Actinomucor, Gongronella, Phycomyces, Mortierella, Pycnoporus and Rhizoctonia. These processes are disclosed in U.S. Pat. No. 4,346,227, filed 5th June 1981, by A. Terahara and M. Tanaka and the compounds thus produced are described in that patent application as M-4, M-4', IsoM-4 and IsoM-4'. These compounds were found to have an ability to inhibit the biosynthesis of cholesterol which is at least comparable with and, in some instances, substantially exceeds that of ML-236B itself.

ML-236B and its derivatives, including the M-4 and M-4' compounds, are thus of therapeutic value for the treatment of hyperlipaemia and the prophylaxis of arteriosclerosis.

BRIEF SUMMARY OF INVENTION

We have now discovered that M-4 and M-4' can also be produced from ML-236B and various derivatives thereof by treatment with a microorganism of the genus Nocardia or a cell-free, enzyme-containing extract thereof. The use of microorganisms of the genus Nocardia has the advantage over the use of those microorganisms disclosed in U.S. Pat. No. 4,346,227 that the Ml-236B compound employed as substrate can be present in the reaction medium to a much higher concentration than when the prior art microorganisms were used. This is most surprising as the ML-236B compounds have been found to possess antifungal and antibiotic properties.

Accordingly, the present invention provides a process for preparing a compound of formula (I):

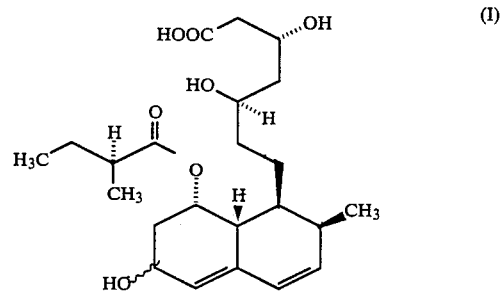

(wherein ⁓OH represents ▬OH or ┉OH), pharmaceutically acceptable salts and esters thereof and the corresponding ring-closed lactones, which process comprises contacting an ML-236B compound selected from the group consisting of ML-236B carboxylic acid, having the formula (II):

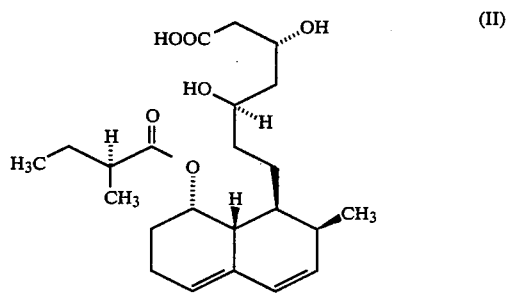

salts and esters thereof and the corresponding ML-236B lactone with a hydroxylation enzyme produced by a microorganism of the genus Nocardia; if necessary, subjecting the resulting product to one or more reactions selected from the group consisting of hydrolysis, salification, esterification and lactonisation; and isolating the product from the reaction mixture.

DETAILED DESCRIPTION OF INVENTION

The compound of formula (I) in which ⁓OH represents ▬OH is called M-4 carboxylic acid and the corresponding salts and esters are known as M-4 carboxylates. The compound of formula (I) in which ⁓OH represents ┉OH is referred to as M-4' carboxylic acid and the corresponding salts and esters are referred to as M-4' carboxylates.

The ring-closed lactones corresponding to the compounds of formula (I) may be represented by the formula (Ia):

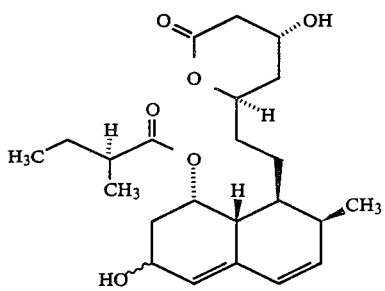

(Ia)

wherein ∿∿ OH represents ━━OH or ┈┈OH and are known as M-4 lactone and M-4' lactone respectively.

The ring-closed lactone corresponding to ML-236B carboxylic acid of formula (II) may be represented by the formula (IIa):

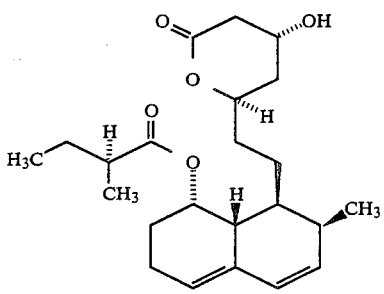

(IIa)

and is known as ML-236B lactone.

Preferred species of the genus Nocardia for use in the process of the present invention are *Nocardia autotrophica, Nocardia asteroides, Nocardia farcinica* and *Norcardia coeliaca*, particularly *Nocardia autotrophica*. Of these species, the following strains are preferred:
Nocardia autotrophica FERM P-6181 (SANK 62781);
Nocardia autotrophica subsp. *canberrica* subsp. nov. FERM P-6182 (SANK 62881);
Nocardia autotrophica subsp. *amethystina* subsp. nov. FERM P-6183 (SANK 62981);
Nocardia autotrophica IFO 12743 (SANK 91279);
Nocardia asteroids IFO 3424 (SANK 62065);
Nocardia farcinica ATCC 3318 (SANK 64265) and
Nocardia coeliaca ATCC 17040 (SANK 63665).

Of the above preferred strains, *Nocardia autotrophica* IFO 12743, *Nocardia asteroides* IFO 3424, *Nocardia farcinica* ATCC 3318 and *Nocardia coeliaca* ATCC 17040 are all known strains which are freely and publicly available from the appropriate culture collection, i.e. the Institute for Fermentation, Osaka, Japan (IFO) or the American Type Culture Collection, U.S.A. (ATCC), under the accession numbers given.

The strains of *Nocardia autotrophica* identified by the accession numbers FERM P-6181, FERM P-6182 and FERM P-6183 are all new strains of the microorganism, newly isolated from soil and deposited on the sixteenth day of October 1981 at the Fermentation Research Institute, Ibaraki-Ken, Japan (FERM).

The morphological and physiological properties of the newly isolated microorganisms were determined using conventional media and the methods described by Shirling and Gottlieb [International Journal of Systematic Bacteriology 16, 313–340 (1966)], together with several supplementary tests. Observations of the culture were made after incubation at 28° C. for 2 weeks. The colour names used were assigned according to the "Guide to Colour Standard" (a manual published by Nippon Shikisai Kenkyusho, Tokyo, Japan). The characteristics of the cultures were compared with those of various known species of actinomycetes described in "The Actinomycetes, Vol. 2" by Waksman, "The ISP Report" by Shirling and Gottlieb, "Bergey's Manual of Determinative Bacteriology", 8th edition and other recent literature concerning the taxonomy of the family Nocardiaceae. The new microorganisms are identified by their FERM accession numbers.

Morphological characteristics

TABLE 1

| | FERM P-6181 | FERM P-6182 | FERM P-6183 |
|---|---|---|---|
| Spore chain morphology | RF | RF | RF |
| Branching | simple | simple | simple |
| Fragmentation | yes | yes | yes |
| Surface structure of segmented hyphae (spores) | smooth | smooth | smooth |
| Other organs | knots, nest-like tangles | knots | none |

RF = rectus-flexibilus

Growth on taxonomic media

All of the new strains showed good growth on a variety of media.

Strain FERM P-6181 had white aerial mycelia on a yellowish-grey to pale yellow-orange growth. In certain media a pale yellow-brown soluble pigment was observed, but only to a small extent.

Strain FERM P-6182 had brown-white to pale yellow-orange aerial mycelia on a greyish-yellow-brown growth. No soluble pigment was observed.

Strain FERM P-6183 had a brown-white to pale yellow-orange growth and brown-violet spots were observed as the cultivation proceeded. Brownish-grey aerial mycelia were present on all media, except for the yeast-malt medium.

The culture properties on the 14th day of cultivation at 28° C. in a variety of media are shown in Table 2. The abbreviations used in the Table are as follows:
G = growth;
AM = aerial mycelium;
R = reverse;
SP = soluble pigment.

TABLE 2

| Media | | FERM P-6181 | FERM P-6182 | FERM P-6183 |
|---|---|---|---|---|
| Yeast-malt agar (ISP 2) | G | Very good, pale yellow-brown (6-7-9) | Very good, brown (6-4-1) | Very good, brown-white (2-9-8) to greyish-red-brown (4-3-5) |
| | AM | Abundant, white | Abundant brownish-white (2-9-7) | Trace, white |
| | R | Dull, yellow-orange (8-8-8) | Brown (4-4-7) | Brown-white (2-9-8) to greyish-red- |

TABLE 2-continued

| Media | | FERM P-6181 | FERM P-6182 | FERM P-6183 |
|---|---|---|---|---|
| | | | | brown (4-3-5) |
| | SP | Yellow-brown (8-7-9) | None | None |
| Oatmeal agar (ISP 3) | G | Good, pale brown (2-8-9) | Very good, pale yellow-orange (2-9-9) | Very good, dark red-brown (4-3-4) |
| | AM | Fair, white | Abundant, pale yellow-brown (2-9-9) | Fair, pale pink (2-8-4) |
| | R | Yellowish-brown (4-7-9) | Pale yellow-brown (4-8-9) | Brown-violet (3-3-2) |
| | SP | Pale yellow-brown (4-8-9) | None | None |
| Starch/ inorganic salt agar (ISP 4) | G | Good, yellowish-grey (2-9-10) | Poor, yellowish-grey (1-9-10) | Very good, brown-violet (3-3-2) |
| | AM | Fair, white | Abundant, pale yellow-orange (2-9-9) | Good, bright brown-grey (2-8-2) |
| | R | Pale yellow (3-9-10) | Pale yellow-orange (2-9-9) | Dark red-brown (4-3-4) |
| | SP | None | None | None |
| Glycerin/ asparagine agar (ISP 5) | G | Good, pale brown (2-8-9) | Good, greyish-yellow-brown (4-5-7) | Very good, pale brown (2-9-9) to brown-violet (3-3-2) |
| | AM | Abundant, white | Abundant, brown-white (1-8-6) | Abundant, white |
| | R | Pale yellow-brown (6-8-9) | Brown (4-4-6) | Pale yellow-orange (2-9-9) to greyish-red-brown (4-3-6) |
| | SP | Pale yellow-brown (6-9-11) | None | None |
| Tyrosine agar (ISP 7) | G | Very good, pale-yellow-orange (3-8-8) | Very good, greyish-yellow-brown (4-5-7) | Good, greyish-brown (4-6-6) |
| | AM | Abundant, white | Abundant, brown-white (2-9-7) | Trace, white |
| | R | Yellowish-grey (1-9-10) | Bright brown (6-5-7) | Pale yellow-orange (2-9-9) to brown-violet (3-3-2) |
| | SP | Pale yellow-brown (6-7-9) | None | None |
| Sucrose nitrate agar | G | Good, pale yellow-brown (2-9-9) | Poor, pale yellow-brown (2-9-9) | Poor, pale yellow-orange (2-9-9) |
| | AM | Fair, white | Abundant, brown-white (2-9-7) | Fair, white |
| | R | Yellowish-grey (1-9-10) | Brown-white (1-9-6) | Pale yellow-orange (2-9-9) |
| | SP | None | None | None |
| Glucose/ asparagine agar | G | Very good, pale yellow-orange (2-9-9) | Good, greyish yellow-brown (4-5-7) | Very good, pale yellow-orange (2-9-9) to brown-violet (3-3-2) |
| | AM | Fair, white | Abundant, bright brown-white (1-7-6) | Fair, white |
| | R | Pale yellow-brown (4-8-9) | Greyish-red-brown (4-3-6) | Pale yellow-orange (2-9-9) to greyish-red-brown (4-3-6) |
| | SP | Pale yellow-brown (4-8-9) | None | None |
| Nutrient agar | G | Good, yellowish-grey (2-9-10) | Very good, pale yellow-brown (6-8-9) | Good, pale yellow-orange (2-9-9) |
| | AM | Fair, white | Pale yellow-orange (2-9-9) | Trace, white |
| | R | Yellowish-grey (4-9-10) | Pale yellow-brown (6-8-9) | Pale yellow-orange (2-9-9) |
| | SP | None | None | None |
| Water agar | G | Poor, yellowish-grey (1-9-10) | Poor, colourless | Poor, pale yellow-orange (2-9-9) |
| | AM | Fair, white | Abundant, white | Fair, white |

TABLE 2-continued

| Media | | FERM P-6181 | FERM P-6182 | FERM P-6183 |
|---|---|---|---|---|
| Potato/ carrot extract agar | R | Yellowish-grey (1-9-10) | Pale yellow-orange (2-9-9) | Pale yellow-orange (2-9-9) |
| | SP | None | None | None |
| | G | Poor, yellowish-grey (1-9-10) | Poor, colourless | Poor, pale yellow-orange (2-9-9) |
| | AM | Fair, white | Fair, white | Fair, white |
| | R | Yellowish-grey (1-9-10) | Pale yellow-orange (2-9-9) | Pale yellow-orange (2-9-9) |
| | SP | None | None | None |

Physiological properties

The physiological properties of the new strains are shown in Table 3. The test for melanoid pigment formation was carried out in three media, as follows:
Medium 1: Tryptone-yeast extract broth (ISP 1);
Medium 2: Peptone-yeast extract-iron agar (ISP 6);
Medium 3: Tyrosine gear (ISP 7).

TABLE 3

| | FERM P-6181 | FERM P-6182 | FERM P-6183 |
|---|---|---|---|
| Nitrate reduction | − | − | − |
| Starch hydrolysis | − | − | − |
| Urea decomposition | + | − | + |
| Lysozyme resistance | − | + | − |
| Melanoid pigment formation | | | |
| Medium 1 | − | − | − |
| Medium 2 | − | − | − |
| Medium 3 | − | − | − |
| Acid production from | | | |
| arabinose | + | − | + |
| xylose | + | − | + |
| raffinose | + | − | NG |

− = negative;
+ = positive;
NG = no growth.

Utilisation of carbohydrates

The utilisation of carbohydrates by the new strains is shown in Table 4. The medium used was Pridham-Gottlieb agar (ISP 9) and determination was made after cultivation at 28° C. for 14 days.

TABLE 4

| | FERM P-6181 | FERM P-6182 | FERM P-6183 |
|---|---|---|---|
| D-Glucose | + | + | + |
| D-Arabinose | + | − | + |
| D-Xylose | + | − | + |
| D-Fructose | + | + | + |
| L-Rhamnose | + | − | ± |
| Inositol | + | + | + |
| Sucrose | + | − | − |
| Raffinose | + | − | − |
| D-Mannitol | + | + | + |
| Control | − | − | − |

+ = utilised;
± = slightly utilised;
− = not utilised.

Cell wall analysis

Paper chromatographic analyses were performed on acid hydrolyzates of each of the three new strains, following the method of B. Becker et al. [Applied Microbiology, 13, 236 (1965)] and that of M. P. Lechevalier et al. ["The Actinomycetales" by H. Prauser, 311 (1970)]. Meso-2,6-diaminopimelic acid was found in the cell walls and arabinose and galactose were found as saccharide components of the whole cell, thus confirming that each of the strains had cellular components of the type IV-A.

The results of these taxonomic studies demonstrate that all strains belong to the genus Nocardia. Of the known species of Nocardia, the characteristics of the new strains are most closely related to those of Nocardia autotrophica [International Journal of Systematic Bacteriology, 30, 337 (1980)[, except only for the differences shown in Table 5. In the Table, symbols and abbreviations are as given in the corresponding Tables 1-4.

TABLE 5

| TEST | | FERM P-6181 | FERM P-6182 | FERM P-6183 | Nocardia autotropnica |
|---|---|---|---|---|---|
| Growth colours | AM | white | white to pale yellow-orange | white to brownish-grey | white to pale yellow |
| | G | yellowish-grey to pale yellow-orange | greyish-yellow-brown | brown-violet | pale yellow to yellowish-grey |
| Decomposition of urea | | + | − | + | + |
| Resistance to lysozyme | | − | + | − | − |
| Acid production from: | | | | | |
| arabinose | | + | − | + | + |
| xylose | | + | − | + | + |
| raffinose | | + | − | NG | − |
| Utilization of: | | | | | |
| arabinose | | + | − | + | + |
| xylose | | + | − | + | + |
| rhamnose | | + | − | ± | + |

TABLE 5-continued

| TEST | FERM P-6181 | FERM P-6182 | FERM P-6183 | Nocardia autotropnica |
|---|---|---|---|---|
| sucrose | + | − | − | + |
| raffinose | + | − | − | + |

Strain FERM P-6181 and *Nocardia autotrophica* resemble each other in their morphological, cultural and physiological characteristics and it was thus concluded that this strain belonged to the species *Nocardia autotrophica*.

Strain FERM P-6182 differed from *Nocardia autotrophica* in its decomposition of urea, its resistance to lysozyme, its acid production from carbohydrates and its utilisation of carbohydrates. However, these differences are not sufficient that strain FERM P-6182 should be considered a new species; it is therefore regarded as a new subspecies of *Nocardia autotrophica*. This strain was accordingly named as *Nocardia autotrophica* subsp. canberrica subsp. nov..

Strain FERM P-6183 differed from *Nocardia autotrophica* in its growth colour and utilisation of rhamnose, sucrose and raffinose. These differences likewise were not sufficient that this strain should be considered to be a new species and it is therefore regarded as a subspecies of *Nocardia autotrophica*. It has been named *Nocardia autotrophic* subsp. *amethystina* subsp. nov.

As with all microbial strains, the new strains FERM P-6181, FERM P-6182 and FERM P-6183 are unstable in their properties and are readily mutated by such artificial mutating agents as ultraviolet radiation, high frequency electromagnetic waves, nuclear radiation and chemical mutating agents. Any mutants obtained from these strains and possessing the desired activities can be employed in the process of the present invention.

Of the various microorganisms of the genus Nocardia which can be employed in the process of the invention, we particularly prefer to employ the three new strains, that is to say *Nocardia autotrophica* FERM P-6181, *Nocardia autotrophica* subsp. *canberrica* FERM P-6182 or *Nocardia autotrophica* subsp. *amethystina* FERM P-6183.

The enzymatic hydroxylation process of the present invention can be effected by contacting the ML-236B compound with the chosen microorganism of the genus Nocardia or with a cell-free, enzyme-containing extract thereof.

This process of the invention is preferably carried out in one of three ways:

(a) adding the starting ML-236B compound to the culture medium during the cultivation of the converting microorganism and then continuing with the cultivation;

(b) collecting a culture of the converting microorganism and contacting the collected cells with the starting ML-236B compound; or (c) preparing a cell-free, enzyme-containing extract from the cells of the converting microorganism and contacting this extract with the starting ML-236B compound.

Cultivation of the converting microorganism of the genus Nocardia can be carried out by conventional means in a conventional culture medium containing nutrients well known for use with such microorganisms. Thus, as is well known, such culture media contain sources of assimilable carbon and of assimilable nitrogen and often inorganic salts. Examples of sources of assimilable carbon include glucose, sucrose, starch, glycerin, millet jelly, molasses and soybean oil. Examples of sources of assimilable nitrogen include soybean solids (including soybean meal and soybean flour), wheat germ, meat extracts, peptone, corn steep liquor, dried yeast and ammonium salts, such as ammonium sulphate. If required, inorganic salts, such as sodium chloride, potassium chloride, calcium carbonate or phosphates, may also be included. Also, if desired, other additives capable of promoting the production of hydroxylation enzymes may be employed in appropriate combinations. The particular cultivation technique is not critical to the process of the invention and any techniques conventionally used for the cultivation of microorganisms may equally be employed with the present invention. In general, of course, the techniques employed will be chosen having regard to industrial efficiency. Thus, liquid culture is generally preferred and the deep culture method is most convenient from the industrial point of view.

Cultivation will normally be carried out under aerobic conditions and at a temperature within the range from 20° to 37° C., more preferably from 26° to 28° C.

Method (a) is carried out by adding the starting ML-236B compound to the culture medium in the course of cultivation. The precise point during the cultivation at which the starting compound is added will vary depending upon the cultivation equipment, composition of the medium, temperature of the culture medium and other factors, but it is preferably at the time when the hydroxylation capacity of the microorganism begins to increase and this is usually 2 or 3 days after beginning cultivation of the microorganism. The amount of the ML-236B compound added is preferably from 0.01 to 5.0% by weight of the medium, more preferably from 0.05 to 0.5%, e.g. from 0.05 to 0.1% by weight. After addition of the ML-236B compound, cultivation is continued aerobically, normally at a temperature within the ranges proposed above. Cultivation is normally continued for a period of from 3 to 5 days after addition of the ML-236B compound.

In method (b), cultivation of the microorganism is first carried out under conditions such as to achieve its maximum hydroxylation capacity; this capacity usually reaches a maximum between 4 and 5 days after beginning the cultivation, although this period is variable, depending upon the nature and temperature of the medium, the species of microorganism and other factors. The hydroxylation capacity of the culture can be monitored by taking samples of the culture at suitable intervals, determining the hydroxylation capacity of the samples by contacting them with an ML-236B compound under standard conditions and determining the quantity of M-4 and M-4' compound obtained and plotting this capacity against time as a graph. When the hydroxylation capacity has reached its maximum point, cultivation is stopped and the microbial cells are collected. This may be achieved by subjecting the culture to centrifugal separation, filtration or similar known separation methods. The whole cells of the cultivating microorganism thus collected are preferably then washed with a suitable washing liquid, such as physiological saline or an appropriate buffer solution.

Contact of the collected cells of the microorganism of the genus Nocardia with the ML-236B compound is generally effected in an aqueous medium, for example in a phosphate buffer solution at a pH value of from 5 to 9. The reaction temperature is preferably within the range from 20° to 45° C., more preferably from 25° to 30° C. The concentration of the ML-236B compound in the reaction medium is preferably within the range from 0.01 to 5.0% by weight. The time allowed for the reaction is preferably from 1 to 5 days, although this may vary depending upon the concentration of the ML-236B compound in the reaction mixture, the reaction temperature, the hydroxylation capacity of the microorganism (which may, of course, vary from species to species and will also, as explained above, depend upon the cultivation time) and other factors.

The cell-free, enzyme-containing extract employed in method (c) may be obtained by breaking down the whole cells of the microorganism obtained as described in relation to method (b) by physical or chemical means, for example by grinding or ultrasonic treatment to provide a disintegrated cellular mass or by treatment with a surface active agent or an enzyme to produce a cellular solution. The resulting cell-free extract is then contacted with the starting ML-236B compound under the same conditions as are described above in relation to method (b).

After completion of the conversion reaction by any of the above methods, the desired compound can be directly isolated, separated or purified by conventional means. For example, separation and purification can be effected by filtering the reaction mixture, extracting the resulting filtrate with a water-immiscible organic solvent (such as ethyl sulphate), distilling the solvent from the extract, subjecting the resulting crude compound to column chromatography, (for example on silica gel or alumina) and eluting the column with an appropriate eluent.

Where the M-4 or M-4' compound converted by the microorganism is not the desired form of that compound, then the product of the conversion reaction may be subjected to one or more further reactions such as hydrolysis, salification, esterification or lactonisation by conventional methods, as described in more detail hereafter. Such additional reactions may be carried out prior to, after or in the course of the separation and purification stages described above, preferably in the course of these stages.

The hydroxylation enzyme active in the process of the invention has no effect in itself on the carboxy group of the ML-236B compound and hence, other factors being equal, ML-263B lactone would give M-4 and/or M-4' lactone, ML-236B carboxylic acid would give M-4 and/or M-4' carboxylic acid, and a salt or ester of ML-236B carboxylic acid would give the same salt or ester of M-4 and/or M-4' carboxylic acid. However, this may be affected by other factors, especially the pH value of the reaction mixture, in a way which is predictable by ordinary laws of chemistry.

The ML-236B starting compound may be the free ML-236B carboxylic acid of formula (II), its corresponding lactone of formula (IIa) or a salt (e.g. metal, amino acid or amine salt) or ester (particularly alkyl ester) thereof.

Preferred metal salts are salts with alkali metals, such as sodium or potassium, salts with alkaline earth metals, such as calcium, or salts with other metals such as magnesium, aluminium, iron, zinc, copper, nickel or cobalt, of which the alkali metal, alkaline earth metal, magnesium and aluminium salts are preferred, the sodium, calcium and aluminium salts being most preferred.

Preferred amino acids to form amino acid salts are basic amino acids, such as arginine, lysine, histidine, α,β-diaminobutyric acid or ornithine.

Preferred amines to form amine salts include t-octylamine, dibenzylamine, dichlorohexylamine, morpholine, alkyl esters of D-phenylglycine and D-glucosamine.

ML-236B esters are preferably the alkyl esters, such as the methyl, ethyl, propyl, isopropyl, butyl, isobutyl or pentyl esters, of which the methyl ester is preferred. However, other esters may be employed if desired.

Of the ML-236B starting materials, the alkali metal salts, e.g. the sodium or potassium salts, are particularly preferred, the sodium salt being most preferred as we have found that this gives the best conversion of the ML-236B compound into the desired M-4 or M-4' compound.

Where the product obtained by the enzymatic hydroxylation process of the present invention is a salt of the carboxylic acid of formula (I), the free carboxylic acid itself can be obtained by adjusting the pH of the filtrate to a value of 4 or less, preferably to a value of from 3 to 4. Any organic acid or mineral acid may be employed, provided that it has no adverse effect upon the desired compound. Examples of the many acids which are suitable include trifluoroacetic acid, acetic acid, hydrochloric acid and sulphuric acid. This carboxylic acid may itself be the desired product or it may be, and preferably is, subjected to subsequent reactions, as described below, optionally after such treatments as extraction, washing and dehydration.

Metal salts of the carboxylic acids of formula (I) may be obtained by contacting a hydroxide, carbonate or similar reactive compound of the chosen metal in an aqueous solvent with the carboxylic acid of formula (I). The aqueous solvent employed is preferably water, or it may be a mixture of water with an organic solvent, preferably an alcohol (such as methanol or ethanol), a ketone (such as acetone), an aliphatic hydrocarbon (such as hexane) or an ester (such as ethyl acetate). We particularly prefer to use a mixture of a hydrophilic organic solvent with water. Such reactions are normally conducted at ambient temperature but they may, if desired, be conducted with heating.

Amine salts of the carboxylic acids of formula (I) may be obtained by contacting an amine in an aqueous solvent with the carboxylic acid of formula (I). Suitable aqueous solvents include water and mixtures of water with alcohols (such as methanol or ethanol), ethers (such as tetrahydrofuran), nitriles (such as acetonitrile) or ketones (such as acetone); we particularly prefer to use aqueous acetone as the solvent for this reaction. The reaction is preferably carried out at a pH of from 7 to 8.5 and preferably at a temperature of ambient or below, more preferably a temperature of from 5° to 10° C. The reaction goes immediately to completion. Alternatively, a metal salt of the carboxylic acid of formula (I) (which may have been obtained as described above) can be dissolved in an aqueous solvent, after which a mineral acid salt (for example the hydrochloride) of the desired amine is added, employing the same reaction conditions as when the amine itself is reacted with the carboxylic acid of formula (I), and the desired product is then obtained by a salt exchange reaction.

Amino acid salts of the carboxylic acids of formula (I) may be obtained by contacting an amino acid in aqueous solution with the carboxylic acid of formula (I). Suitable aqueous solvents include water and mixtures of water with alcohols (such as methanol or ethanol) or ethers (such as tetrahydrofuran). The reaction is preferably carried out with heating, for example at a temperature of from 50° to 60° C.

Esters, preferably alkyl esters, of the carboxylic acids of formula (I) may be obtained by contacting the carboxylic acid of formula (I) with an appropriate alcohol. We prefer to carry out this reaction in the presence of an acid catalyst, for example a mineral acid (such as hydrochloric acid or sulphuric acid), a Lewis acid (for example boron trifluoride) or an ion exchange resin. The solvent employed for this reaction is not critical, provided that it does not adversely affect the reaction; suitable solvents include benzene, chloroform and ethers. Alternatively, the desired product may be obtained by contacting the carboxylic acid of formula (I) with a diazoalkane, in which the alkane moiety may be substitued or unsubstituted. This reaction is usually effected by contacting the acid with an ethereal solution of the diazoalkane. As a further alternative, the ester may be obtained by contacting a metal salt of the carboxylic acid of formula (I) with a halide, preferably an alkyl halide, in a suitable solvent; preferred solvents include dimethylformamide, tetahydrofuran, dimethyl sulphoxide and acetone. All of the reactions for producing esters are preferably effected at about ambient temperature, if required by the nature of the reaction system, the reactions may be conducted with heating.

Lactones of the carboxylic acids of formula (I) may be obtained by contacting the carboxylic acid of formula (I) with a catalytic amount of an acid, which may be organic or inorganic. We prefer to use such organic and mineral acids as trifluoroacetic acid, hydrochloric acid and sulphuric acid. This reaction is preferably effected at about ambient temperature.

Examples of the salts aand esters of the M-4 and M-4' compounds produced by the processes of the invention include those given above as salts and esters of ML-236B, for use as the starting material.

The M-4 and M-4' derivatives thus obtained can be isolated, separated or purified by convention means, for example by adsorption on a carrier (such as active carbon or silica gel), or ion exchange chromatography, or gel filtration by a Sephadex (trade mark) column, or by extraction with an organic solvent, such as an ether, ethyl acetate or chloroform; if desired, and it is normally preferred, a combination of these techniques may be employed.

The M-4 and M-4' isomers can be separated from each other after completion of the conversion reaction or at any appropriate point during the reactions or during the above-described separation or purification processes.

The invention is further illustrated by the following non-limiting Examples.

EXAMPLE 1

Cells of *Nocardia autotrophica* subsp. *amethystina* FERM P-6183 was inoculated from a slant culture by means of a platinum loop into each of twenty 500 ml Erlenmeyer flasks, each containing 100 ml of a culture medium having the following composition (percentages are w/v):

| | |
|---|---|
| Glucose | 1.0% |
| Peptone | 0.2% |
| Meat extract | 0.1% |
| Yeast extract | 0.1% |
| Corn steep liquor | 0.3% |
| Tap water | balance |
| | (pH not adjusted) |

Shaking was then carried out at 26° C. and 220 r.p.m. for 2 days, at which time sodium ML-236B carboxylate was added to a final concentration of 0.05% w/v. Incubation was continued at 26° C. and 220 r.p.m. for a further 5 days.

After completion of the cultivation, the reaction mixture was filtered and the pH of the filtrate was adjusted to a value of 3 by the addition of trifluoroacetic acid. The acidified filtrate was then extracted three times, each with 1 liter of ethyl acetate, to give extracts containing a mixture of M-4 carboxylic acid and M-4' carboxylic acid. Samples of these extracts were taken and subjected to thin layer chromatography on a silica gel plate Art 5715 (manufactured by Merck & Co. Inc.), developed with a 50:50:3 by volume mixture of benzene, acetone and acetic acid. The Rf value of M-4 carboxylic acid was 0.45 and the Rf value of M-4' carboxylic acid was 0.46.

The whole of the remainder of the extract was washed with a saturated solution of sodium chloride, after which there was added an equimolar amount of an ethereal solution of diazomethane, at ambient temperature. The mixture was allowed to stand for 30 minutes, after which it was evaporated to dryness under reduced pressure. The residue was placed on a Lobar column (Si 60, manufactured by Merck & Co. Inc., size A), which was then eluted with a 1:1 by volume mixture of benzene and ethyl acetate. There were obtained separate fractions containing methyl M-4 carboxylic and methyl M-4' carboxylate. These fractions were concentrated by evaporation under reduced pressure, to give 320 mg of methyl M-4 carboxylate and 11 mg of methyl M-4' carboxylate, both in the form of colourless oils.

By replacing the diazomethane in the procedure described above by other appropriate diazoalkanes, other esters of M-4 carboxylic acid and M-4' carboxylic acid can be obtained.

Physical properties of methyl M-4 carboxylate

Nuclear Magnetic Resonance Spectrum (in deuterochloroform, using tetramethylsilane as the internal standard, at 200 MHz), $\delta$ ppm:

0.88 (3H, triples, J=7.3 Hz);
0.89 (3H, doublet, J=6.5 Hz);
1.12 (3H, doublet, J=6.8 Hz);
1.1–1.7 (10H, multiplet);
2.34 (1H, sextet, J=7 Hz);
2.3–2.5 (2H, multiplet);
2.49 (2H, doublet, J=6.4 Hz);
2.58 (1H, multiplet);
3.72 (3H, singlet);
3.78 (1H, multiplet);
4.25 (1H, quintet, J=7 Hz);
4.40 (1H, multiplet);
5.42 (1H, multiplet);
5.56 (1H, multiplet);
5.90 (1H, doublet of doublets, J=9.8 and 5.6 Hz);
5.99 (1H, doublet, J=9.8 Hz).
Mass Spectrum After silylation with N,O-bis(trimethylsilyl)trifluoroacetamide, measurement was made using a D-300 type instrument, manufactured by Nihon Electronic Co.

M/e: 654 (M+), 552, 462, 372, 290, 272, 233, 231.

Ultraviolet Absorption Spectrum (ethanol) $\lambda_{max}$ nm: 230.1, 237.3, 246.4.

Infrared Absorption Spectrum (thin film) $\nu_{max}$ cm$^{-1}$: 3400, 2950, 1730.

Thin layer chromatography

On a silica gel plate Art 5715, manufactured by Merck & Co. Inc., using a 1:1 by volume mixture of benzene and acetone as the developing solvent.

Rf value: 0.88.

Physical properties of methyl M-4' carboxylate

Nuclear Magnetic Resonance Spectrum (in deuterochloroform, using tetramethylsilane as the internal standard, at 60 MHz) δ ppm:
 3.70 (3H, singlet);
 5.50 (1H, broad singlet);
 5.75 (1H, broad singlet);
 5.90 (1H, quartet);
 6.01 (1H, doublet).

Ultraviolet Absorption Spectrum (methanol) $\lambda_{max}$ nm: 230, 238, 246.

Infrared Absorption Spectrum (thin film) $\nu_{max}$ cm$^{-1}$: 3400, 1730.

Mass Spectrum

After silylation with N,N-bis(trimethylsilyl)trifluoroacetamide, measurement was made using a D-300 type instrument manufactured by Nihon Electronic Co.

M/e: 654 (M+).

Elemental Analysis: Calculated for $C_{24}H_{38}O_7$: C, 65.73%; H, 8.73%. Found: C, 65.66%; H, 8.79%.

EXAMPLE 2

The procedures described in Example 1 were repeated, to afford 1.9 liters of a conversion reaction mixture. The pH of this mixture was then adjusted to a value of 3.0 by the addition of trifluoroacetic acid, after which the mixture was extracted three times, each time with 1 liter of ethyl acetate, to give a fraction containing both M-4 carboxylic acid and M-4' carboxylic acid.

The extract was then washed with a saturated solution of sodium chloride, after which it was dried over anhydrous sodium sulphate. A catalytic amount of trifluoroacetic acid was then added to effect lactonisation. The resulting mixture was then washed with a 5% w/v aqueous solution of sodium hydrogen carbonate, after which it was dried over anhydrous sodium sulphate and the evaporated to dryness, to give a lactone fraction.

This lactone fraction was placed on a Lobar column (Si 60, manufactured by Merck & Co. Inc., size A) and eluted with a 7:3 by volume mixture of benzene and acetone, to give separate fractions containing M-4 lactone and M-4' lactone. These fractions were separately recrystallised from ethyl acetate, to give 270 mg of M-4 lactone and 8 mg of M-4' lactone.

Physical properties of M-4 lactone

Nuclear Magnetic Resonance Spectrum (in deuterochloroform, using tetramethylsilane as the internal standard, at 100 MHz) δ ppm:
 4.38 (1H multiplet);
 4.41 (1H, multiplet);
 4.62 (1H, multiplet);
 5.41 (1H, multiplet);
 5.58 (1H, multiplet);
 5.90 (1H, quartet);
 6.01 (1H, doublet).

Ultraviolet Absorption Spectrum (methanol) $\lambda_{max}$ nm: 230, 236.7, 244.6.

Infrared Absorption Spectrum (thin film) $\nu_{max}$ cm$^{-1}$: 3400, 2950, 1725.

Thin Layer Chromatography

On a silica gel plate Art 5715, manufactured by Merck & Co. Inc., using a 50:50:3 by volume mixture of benzene, acetone and acetic acid as the developing solvent.

Rf value: 0.62.

Physical properties of M-4' lactone

Nuclear Magnetic Resonance Spectrum (in deuterochloroform, using tetramethylsilane as the internal standard, at 100 MHz) δ ppm:
 4.25 (1H, multiplet);
 4.60 (1H, multiplet);
 5.50 (1H, multiplet);
 5.75 (1H, multiplet);
 5.90 (1H, quartet);
 6.01 (1H, doublet).

Ultraviolet Absoprtion Spectrum (methanol) $\lambda_{max}$ nm: 230, 237, 245.

Infrared Absorption Spectrum (KBr) $\nu_{max}$ cm$^{-1}$: 3500, 1720.

Mass Spectrum: M/e: 406 (M+), 304, 286.

Optical Rotation: $[\alpha]_D^{22} = +310.9°$ (c=0.66, methanol).

Melting point: 141°–143° C.

Elemental analysis: Calculated for $C_{23}H_{34}O_6$: C, 67.95%; H, 8.43%. Found: C, 68.05%; H, 8.37%

Thin layer chromatography:

On a silica gel plate Art 5715, manufactured by Merck & Co. Inc., using a 1:1 by volume mixture of benzene and acetone as the developing solvent.

Rf value: 0.64.

EXAMPLE 3

The procedure described in Example 1 was repeated up to and including extraction with three portions of ethyl acetate to give an extract containing both M-4 carboxylic acid and M-4' carboxylic acid.

This extract was then immediately transferred into a 5% w/v aqueous solution of sodium hydrogen carbonate, and the pH of the mixture was adjusted to a value of 7.0 by the addition of 2N hydrochloric acid. The mixture was then adsorbed on a Diaion HP-20 column (manufactured by Mitsubishi Chemical Industries). The column was washed with water and then eluted with 50% v/v aqueous acetone to give a fraction containing sodium M-4 carboxylate. This was freeze-dried, to give 200 mg of sodium M-4 carboxylate.

Physical properties of sodium M-4 carboxylate

Nuclear magnetic resonance spectrum (in deuteromethanol, using tetramethylsilane as the internal standard, at 200 MHz) δ ppm:
 0.91 (3H, triplet, J=7.5 Hz);
 0.92 (3H, doublet, J=7 Hz);
 1.12 (3H, doublet, J=7 Hz);
 1.1–1.8 (10H, multiplet);
 2.25 (1H, doublet of doublets, J=15 & 7.6 Hz);
 2.34 (1H, doublet of doublets, J=15 & 5.5 Hz);
 2.2–2.4 (3H, multiplet);
 2.48 (1H, multiplet);
 3.68 (1H, multiplet);
 4.07 (1H, multiplet);
 4.28 (1H, multiplet);
 5.36 (1H, multiplet);

5.48 (1H, doublet of doublets, J=3 & 2 Hz);
5.88 (1H, doublet of doublets, J=9.6 & 5.3 Hz);
5.98 (1H, doublet, J=9.8 Hz).

Ultraviolet absorption spectrum (methanol) $\lambda_{max}$ nm: 230.0, 237.2, 245.0.

Infrared absorption spectrum (KBr) $\nu_{max}$ cm$^{-1}$: 3400, 2900, 1725, 1580.

Thin layer chromatography:

On a silica gel plate Art 5715, manufactured by Merck & Co. Inc., using a 50:50:3 by volume mixture of benzene, acetone and ethyl acetate as the developing solvent.

Rf value: 0.45.

EXAMPLE 4

The procedures described in Examples 1-3 were repeated but using the strain *Nocardia autotrophica* FERM P-6181 in place of *Nocardia autotrophica* subsp. *amethystina* FERM P-6183; there were obtained: 150 mg of methyl M-4 carboxylate; 37 mg of methyl M-4' carboxylate; 140 mg of M-4 lactone; 30 mg of M-4' lactone; and 110 mg of sodium M-4 carboxylate. In eace case, the products had properties identical with the respective compounds obtained in Examples 1-3.

EXAMPLE 5

Loopfulls of a culture of *Nocardia autotrophica* subsp. *canberrica* FERM P-6182 were inoculated into each of twenty 500 ml Erlenmeyer flask, each containing 100 ml of a medium having the following composition (percentages are w/v):

| | |
|---|---|
| Glycerin | 0.5% |
| Sucrose | 2.0% |
| Soybean meal | 1.0% |
| Pressed yeast | 1.0% |
| Corn steep liquor | 0.5% |
| Cobalt chloride | 0.001% |
| Tap water | balance (pH 7.0). |

Shaking culture was continued at 26° C. at 220 r.p.m. for 2 days, at which time sodium ML-236B carboxylate was added to a final concentration of 0.05% w/v. Cultivation was then continued at 26° C. and 220 r.p.m. for a further 5 days. The conversion reaction mixture was then filtered and the pH of the filtrate was adjusted to a value of 3.0 by addition of hydrochloric acid. The mixture was then extracted three times, each time with 1 liter of ethyl acetate, to afford an extract containing both M-4 carboxylic acid and M-4' carboxylic acid, demonstrated by thin layer chromatography to be identical with the respective products of Example 1.

This extract was then further treated as described in Example 1, to give 180 mg of methyl M-4 carboxylate and 110 mg of methyl M-4' carboxylate.

EXAMPLE 6

The procedure described in Example 5 was repeated up to and including preparation of the extract containing M-4 carboxylic acid and M-4' carboxylic acid. This extract was then treated as described in Example 2, to give 170 mg of M-4 lactone and 90 mg of M-4' lactone.

EXAMPLE 7

Loopfulls of a culture of *Nocardia autotrophica* subsp. *amethystina* FERM P-6183 were inoculated into ten 500 ml Erlenmeyer flasks, each containing 100 ml of a medium having the following composition (percentages are w/v):

| | |
|---|---|
| Glucose | 1.0% |
| Peptone | 0.2% |
| Meat extract | 0.1% |
| Yeast extract | 0.1% |
| Tap water | balance (pH not adjusted). |

Shaking culture was then carried out at 26° C. and 220 r.p.m. for 5 days, after which whole microbial cells were collected by centrifugal separation. The collected cells were washed with a 0.1M phosphate buffer solution (pH 7.0) and then again collected and suspended in 900 ml of 0.1M phosphate buffer solution. To this suspension was added sodium ML-236B carboxylate to a concentration of 0.5 g/100 ml, and the mixture was incubated at 26° C. and 220 r.p.m. for 5 days. At the end of this time, the conversion mixture was filtered and its pH was adjusted to a value of 3.0 by addition of hydrochloric acid. The mixture was then extracted three times, each time with 1 liter of ethyl acetate, to afford an extract containing M-4 carboxylic acid and M-4' carboxylic acid, identified by thin layer chromatography and shown to be the same as the respective products of Example 1.

EXAMPLE 8

The procedure described in Example 2 was repeated, except that the microorganisms listed in Table 6 were employed; the amount of M-4 lactone obtained is as shown in the Table.

TABLE 6

| Microorganism | Amount (mg) of M-4 lactone |
|---|---|
| *Nocardia farcinica* ATCC 3318 | 7 |
| *Nocardia coeliaca* ATCC 17040 | 5 |
| *Nocardia autotrophica* IFO 12743 | 10 |
| *Nocardia asteroides* IFO 3424 | 15 |

EXAMPLE 9

Cells of *Nocardia autotrophica* subsp. *amethystina* FERM P-6183 were inoculated from a slant culture by means of a platinum loop into each of twenty 500 ml Erlenmeyer flasks, each containing 100 ml of a culture medium having the composition given in Example 7. Shaking culture was then carried out at 26° C. and 220 r.p.m. for 2 days, at which time sodium ML-236B carboxylate was added to a final concentration of 0.4% w/v. Incubation was continued at 26° C. and 220 r.p.m. for a further 5 days. The procedure described in Example 2 was then repeated, giving 2.9 g of M-4 lactone.

We claim:

1. A process for preparing a compound of formula (I):

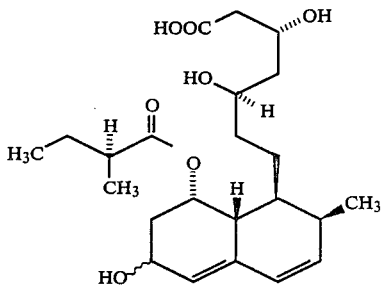

wherein ⁓ OH represents ━ OH or ⫶⫶⫶ OH, pharmaceutically acceptable salts and esters thereof and the corresponding ring-closed lactones, which process comprises contacting an ML-236B compound selected from the group consisting of ML-236B carboxyic acid, salts and esters thereof and the corresponding ML-236B lactone with a hydroxylation enzyme produced by a microorganism of the genus Nocardia to produce the hydroxylated ML-236B compound of the formula (I).

2. A process as claimed in claim 1, wherein said ML-236B compound is contacted with said enzyme by cultivating a microorganism of the genus Nocardia in a medium containing said ML-236B compound.

3. A process as claimed in claim 2, wherein said microorganism is a species selected from the group consisting of *Nocardia autotrophica, Nocardia asteroides, Nocardia farcinica* and *Nocardia coeliaca.*

4. A process as claimed in claim 2, wherein said microorganism is selected from the group consisting of:
*Nocardia autotrophica* FERM P-6181
*Nocardia autotrophica* subsp. *canberrica* FERM P-6182
*Nocardia autotrophica* subsp. *amethystina* FERM P-6183
*Nocardia autotrophica* IFO 12743
*Nocardia asteroides* IFO 3424
*Nocardia farcinica* ATCC 3318 and
*Nocardia coeliaca* ATCC 17040.

5. A process as claimed in claim 2, wherein said microorganism is selected from the group consisting of:
*Nocardia autotrophica* FERM P-6181
*Nocardia autotrophica* subsp. *canberrica* FERM P-6182
*Nocardia autotrophica* subsp. *amethystina* FERM P-6183
*Nocardia autotrophica* IFO 12743
*Nocardia asteroides* IFO 3424.

6. A process as claimed in claim 2, wherein said microorganism is selected from the group consisting of:
*Nocardia autotrophica* FERM P-6181
*Nocardia autotrophica* subsp. *canberrica* FERM P-6182 and
*Nocardia autotrophica* subsp. *amethystina* FERM P-6183.

7. A process as claimed in claim 1, wherein said ML-236B compound is contacted with said enzyme by contacting whole cells of a microorganism of the genus Nocardia with said ML-236B compound.

8. A process as claimed in claim 7, wherein said microorganism is a species selected from the group consisting of *Nocardia autotrophica, Nocardia asteroides, Nocardia farcinica* and *Nocardia coeliaca.*

9. A process as claimed in claim 7, wherein said microorganism is selected from the group consisting of:
*Nocardia autotrophica* FERM P-6181
*Nocardia autotropica* subsp. *canberrica* FERM P-6182
*Nocardia autotrophica* subsp. *amethystina* FERM P-6183
*Nocardia autotrophica* IFO 12743
*Nocardia asteroides* IFO 3424
*Nocardia farcinica* ATCC 3318 and
*Nocardia coeliaca* ATCC 17040.

10. A process as claimed in claim 7, wherein said microorganism is selected from the group consisting of:
*Nocardia autotrophica* FERM P-6181
*Nocardia autotrophica* subsp. *canberrica* FERM P-6182
*Nocardia autotrophica* subsp. *amethystina* FERM P-6183
*Nocardia autotrophica* IFO 12743
*Nocardia asteroides* IFO 3424.

11. A process as claimed in claim 7, wherein said microorganism is selected from the group consisting of:
*Nocardia autotrophica* FERM P-6181
*Nocardia autotrophica* subsp. *canberrica* FERM P-6182 and
*Nocardia autotrophica* subsp. *amethystina* FERM P-6183.

12. A process as claimed in claim 1, wherein said ML-236B compound is contacted with said enzyme by contacting said compound with a cell-free, enzyme-containing extract of a microorganism of the genus Nocardia.

13. A process as claimed in claim 12, wherein said microorganism is a species selected from the group consisting of *Nocardia autotrophica, Nocardia asteroides, Nocardia farcinica* and *Nocardia coeliaca.*

14. A process as claimed in claim 12, wherein said microorganism is selected from the group consisting of:
*Nocardia autotrophica* FERM P-6181
*Nocardia autotrophica* subsp. *canberrica* FERM P-6182
*Nocardia autotrophica* subsp. *amethystina* FERM P-6183
*Nocardia autotrophica* IFO 12743
*Nocardia asteroides* IFO 3424
*Nocardia farcinica* ATCC 3318 and
*Nocardia coeliaca* ATCC 17040.

15. A process as claimed in claim 12, wherein said microorganism is selected from the group consisting of:
*Nocardia autotrophica* FERM P-6181
*Nocardia autotrophica* subsp. *canberrica* FERM P-6182
*Nocardia autotrophica* subsp. *amethystina* FERM P-6183
*Nocardia autotrophica* IFO 12743
*Nocardia asteroides* IFO 3424.

16. A process as claimed in claim 12, wherein said microorganism is selected from the group consisting of:
*Nocardia autotrophica* FERM P-6181
*Nocardia autotrophica* subsp. *canberrica* FERM P-6182 and
*Nocardia autotrophica* subsp. *amethystina* FERM P-6183.

17. A process as claimed in claim 1, wherein said microorganism is selected from the group consisting of *Nocardia autotrophica* FERM P-6181, Nocardia autotrophica subsp. *canberrica* FERM P-6182 and *Nocardia autotrophica* subsp. *amethystina* FERM P-6183.

18. A process as claimed in claim 1, wherein there is produced an M-4 compound in which ⁓ OH represents ━ OH.

19. A process as claimed in claim 17, wherein there is produced an M-4 compound in which ⁓OH represents —OH.

20. A process as claimed in claim 1, wherein there is produced an M-4' compound in which ⁓OH represents ⁙⁙OH.

21. A process as claimed in claim 17, wherein there is produced an M-4' compound in which ⁓OH represents ⁙⁙OH.

22. A process as claimed in claim 1, wherein there is produced the sodium salt of said compound of formula (I).

* * * * *